United States Patent [19]

Matsuda et al.

[11] 4,046,791

[45] Sept. 6, 1977

[54] METHOD FOR PRODUCING MONOALKYL-TIN-TRIHALIDES

[75] Inventors: Sumio Matsuda, Ibaraki; Hajime Kudara, Shiga, both of Japan

[73] Assignee: Chugoku Marine Paints, Ltd., Hiroshima, Japan

[21] Appl. No.: 613,155

[22] Filed: Sept. 15, 1975

[30] Foreign Application Priority Data

Mar. 20, 1975 Japan ................................. 50-33706
Apr. 9, 1975 Japan ................................. 50-43533

[51] Int. Cl.² ............................................. C07F 7/22
[52] U.S. Cl. ............................................. 260/429.7
[58] Field of Search ................................. 260/429.7

[56] References Cited

U.S. PATENT DOCUMENTS

| | | | |
|---|---|---|---|
| 2,625,559 | 1/1953 | Smith | 260/429.7 |
| 3,085,102 | 4/1963 | Yatagai | 260/429.7 |
| 3,340,283 | 9/1967 | Gloskey | 260/429.7 |
| 3,414,595 | 12/1968 | Oakes | 260/429.7 |
| 3,519,667 | 7/1970 | Molt et al. | 260/429.7 |
| 3,824,264 | 7/1974 | Bulten | 260/429.7 |

FOREIGN PATENT DOCUMENTS 1,079,641   8/1967   United Kingdom

OTHER PUBLICATIONS

Chemical Abstracts, vol. 64, 8240a (1966).

*Primary Examiner*—Helen M. S. Sneed
*Attorney, Agent, or Firm*—John C. Smith, Jr.

[57] ABSTRACT

Monoalkyl-tin-trihalides are prepared in a high yield by a method in which a stannous halide reacts with an alkyl halide in an organic solvent in the presence of a catalytic substance selected from the group consisting of magnesium, iodine, bromine, Grignard reagents and a mixture of two or more of the above-mentioned substances, the organic material being selected from liquid alcohols, tetrahydrofuran, liquid organic acids, liquid esters of organic acids, liquid ketones, liquid hydrocarbons and mixtures of two or more of the above-mentioned compounds, and the resultant monoalkyl-tin-trihalide is isolated from the reaction mixture.

8 Claims, No Drawings

METHOD FOR PRODUCING MONOALKYL-TIN-TRIHALIDES

The present invention relates to a method for producing monoalkyl-tin-trinhalides. More particularly, it relates to a process for producing monoalkyl-tin-trihalides during a short reaction time, at a high yield.

The monoalkyl-tin-trihalides of the formula $RSnX_3$ wherein R represents an alkyl radical and X represents a halogen atom are useful as constituents to be mixed with a dimethyl tin compound so as to prepare an excellent stabilizer for polyvinyl chloride. In addition, these compounds can be used as an intermediate of organotin compounds.

It is known that the monoalkyl-tin-trihalide can be produced from stannic chloride and a Grignard reagent by way of a Grignard reaction, from stannous chloride or bromide and a halogenated alkyl compound by way of a catalytic reaction in the presence of a catalyst consisting of an organoantimony compound, or from tetraalkyl lead and stannous tetrachloride by way of a metal exchange reaction.

However, it is also known that the above-mentioned conventional methods are disadvantageous in that they have a low yield of the desired product, a long reaction time and a high cost. For example, the method utilizing the Grignard reaction has the following disadvantages.

1. A plurality of types of alkyl-tin-halides are produced since it is very difficult to produce only monoalkyl-tin-halide in a high yield.
2. A time period of 30 to 70 hours is required to complete the reaction.
3. It is difficult to economically recover solvents used in the method.

The catalytic method using the organoantimony compound has the following disadvantages.

1. The completion of the reaction requires 30 to 70 hours.
2. The yield of the desired product is relatively low.
3. There is an economical disadvantage in that the organoantimony compound which is very expensive must be used as the catalyst.

The method utilizing the metal exchange reaction has the following defects.

1. The yield of the desired product in a single exchange operation is very low.
2. The resultant product includes therein a plurality of alkyl-tin-halides, and, therefore, the desired monoalkyl-tin-trihalide must be isolated from the other products (for example, dialkyl-tin-dihalide).
3. The starting material, tetraalkyl lead, is highly toxic to the human body, and, therefore, there is a problem regarding the safe handling of said starting material.

An object of the present invention is to provide a method for producing monoalkyl-tin-trihalide in a very high yield close to 100%, by a single reaction operation.

Another object of the present invention is to provide a method for producing monoalkyl-tin-trihalide within a relatively short time, at a relatively low cost.

These and other objects of the present invention which will become apparent from the detailed description below, can be attained by the method of the present invention.

The method of the present invention for producing monoalkyl-tin-trihalide comprises reacting a stannous halide with an alkyl halide in an organic solvent selected from the group consisting of liquid alcohols, tetrahydrofuran, liquid organic acids, liquid esters of organic acids, liquid ketones, liquid hydrocarbons and mixtures of two or more of the above-mentioned compounds, in the presence of a catalytic substance selected from the group consisting of magnesium, iodine, bromine, Grignard reagents, and mixtures of two or more of the above-mentioned substances, and isolating said resulting monoalkyl-tin-trihalide from the reaction mixture.

In the method of the present invention, there is no limitation in type of alkyl group and of the halogen atom in the alkyl halide. However, it is preferable that the alkyl halide is of the formula RX wherein R represents an alkyl group having 1 through 8 carbon atoms and X represents either a chlorine or bromine atom. That is, the alkyl halide is preferably selected from the group consisting of methyl chloride, ethyl chloride, n- and iso-propyl chlorides, n-, iso-, sec- and tert-butyl chlorides, n-heptyl chloride, n-hexyl chloride, n-octyl chloride, methyl bromide, ethyl bromide, n- and iso-propyl bromides, n-, iso-, sec- and tert-butyl bromides, n-heptyl bromide, n-hexyl bromide and, n-octyl bromide.

The stannous halide is preferably of the formula $SnX_2$ wherein X is either chlorine or a bromine atom. That is, the stannous halides may be either stannous chlorides or stannous bromides.

In the method of the present invention, the alkyl halide to be reacted with stannous halide is used in an amount by mole not smaller than that of the stannous halide. In this preparation, in order to improve the yield of the desired monoalkyl-tin-trihalide, it is preferable that the alkyl halide is used in an amount by mole larger than that of the stannous halide. If the alkyl halide is used in an amount by mole smaller than that of the stannous halide, there is a tendency for the yield of the resultant monoalkyl-tin-trihalide to be decreased and to produce undesired by-products, for example, dialkyl-tin-dihalide.

In the method of the present invention, it is desirable that the organic solvent be inert with regard to the stannous halide, alkyl halide and the catalytic substance, and it is preferable that the solvent has a boiling point of 60° through 200° C under a pressure of 1 atom.

In the organic solvent, the liquid alcohols usable for the method of the present invention may be selected from aliphatic alcohols having 1 through 8 carbon atoms, for example, methyl alcohol, ethyl alcohol, propyl alcohols, butyl alcohols, amyl alcohols or octyl alcohols. The liquid organic acids may be selected from aliphatic acids having 1 through 8 carbon atoms, for example, formic acid, acetic acid, propionic acid, butylic acid, caproic acid, and caprylic acid.

The liquid esters of organic acids may be selected from aliphatic esters consisting of an alkyl moiety having 1 through 8 carbon atoms and an aliphatic acid moiety having 1 through 8 carbon atoms, for example, methyl formate, ethyl formate, propyl formate, n- and iso-butyl formate, n-amyl formate, methyl acetate, ethyl acetate, n- and iso-propyl acetates, n-, iso- and sec-butyl acetates, n- and iso-amyl acetates, 2-ethylbutyl acetate, methyl amyl acetate and sec-hexyl acetate. The liquid ketone may be selected from aliphatic ketones having 3 through 8 carbon atoms, for example, acetone, methyl ethyl ketone, methyl-butyl ketones methyl-amyl ketones, diethyl ketone, ethyl-butyl ketones or dipropyl ketones. The liquid hydrocarbon may be selected from aliphatic hydrocarbons having 6 through 10 carbon atoms, for example, n-hexane, 2,2-dimethyl butane, isohexane, n-heptane, n-octane, isooctane and n-decane; cycloaliphatic hydrocarbons having 6 through 9 carbon atoms, for example, cyclohexane and methyl cyclohexane; and aromatic hydrocarbons having 6 through 9 carbon atoms, for example, benzene, toluene, p-, m- and o-xylenes and ethyl benzene.

A mixture of tetrahydrofuran and toluene is preferable as the solvent for the method of the present invention. In this type of solvent, it is preferable that tetrahydrofuran and toluene are mixed in the same amount by weight as each other.

The organic solvent is used in an amount of 80 to 200% based on the sum of the weights of the stannous halide and the alkyl halide.

In the method of the present invention, the reaction of the stannous halide and the alkyl halide is effected in the presence of a catalytic substance selected from the group consisting of magnesium, iodine, bromine, Grignard reagents and mixtures of two or more of the above-mentioned substances.

The magnesium may be suspended in the form of fine particles or finely divided foil in the solvent. The iodine may be suspended in the form of particles, grains or lumps in the solvent. The bromine and Grignard reagents may be dissolved or emulsified in the solvent.

In order to carry out the reaction at a proper reaction rate and in at an economical cost, it is preferable that the catalytic substance is presented in an amount of 2 through 10%, more preferably 3 through 5%, based on the sum of the weights of the stannous halide and the alkyl halide in the reaction mixture. Also, it is preferable that the reaction is carried out at a temperature of 150° through 250° C, more preferably, 220° through 225° C under either an ambient pressure or a pressurized pressure, for example, 30 kg/cm$^2$ or lower, in response to the types of the solvent, the stannous halide, alkyl halide and the catalytic substance. Generally, if the reaction temperature is lower than 150° C, the reaction rate may be very low and this results in an economical disadvantage. A reaction temperature higher than 250° C may cause an undesirably high pressure in the reaction system and the production of undesirable by-products. Very high pressure of the reaction system, for example, higher than 80 kg/cm$^3$, may cause difficulty in the reaction operation. The reaction mixture is maintained under the above-mentioned conditions for a time long enough to complete the reaction, for example, 1 to 3 hours, while the reaction mixture is stirred.

After the completion of the reaction, solid substances in the reaction mixture, for example, solid catalytic substances, are removed by way of fitration or centrifugation operation.

The reaction mixture containing therein no solid substance is subjected to a distillation under a predetermined condition in response to the type of the solvent and the reaction components, in order to remove the solvent, the catalytic substance and non-reacted alkyl halide and stannous halide from the reaction mixture. Generally, the distillation is carried out at a temperature up to 150° C under a reduced pressure of 60 through 50 mmHg. The resultant distillation residue consists of a mixture of about 90% of the monoalkyl-tin-trihalide and about 10% of the solvent. Usually, the mixture is sent to the next step. However, if necessary, the solvent can be removed by way of drying under reduced pressure.

In the following examples, preferred embodiments of the present invention are described, which embodiments do not limit the scope of the present invention. Unless otherwise stated, percentages in the examples are by weight.

EXAMPLE 1

A reaction mixture was prepared by dissolving 40 g of stannous chloride (SnCl$_2$) in a mixture solvent consisting of 30 g of tetrahydrofuran and 20 g of toluene, and then adding 5 g of iodine, 0.3 g of magnesium and 40 g of methyl chloride (CH$_3$Cl). The reaction mixture thus prepared was charged into a closed vessel and heated at a temperature between 190° and 210° C for approximately 3 hours while it was stirred. After the completion of the reaction, the reaction mixture was filtered to remove solid substances therefrom and was distilled at a temperature of 15° C under a reduced pressure of 60 mmHg. A portion of the distillation residue was subjected to a gas chromatographic analysis. It was determined by said analysis that monomethyl-tin-trichloride (CH$_3$SnCl$_3$) was prepared in yield of 95%, based on the theoretical yield.

EXAMPLE 2

Procedures identical to those in Example 1 were repeated, except that ethyl acetate was used instead of tetrahydrofuran. The yield of monomethyl-tin-trichloride was 80%.

EXAMPLE 3

A reaction mixture was prepared from 40 g of stannous chloride, 50 g of tetrahydrofuran, 30 g of toluene, 80 g of n-butyl chloride, 6 g of iodine and 1 g of magnesium. The reaction mixture was heated at a temperature of 210° to 220° C under a pressure of 45 kg/cm$^2$ for 3 hours. The reaction mixture was subjected to the same after-treatment as that in Example 1. By a gas chromatographic analysis of the distillation residue, it was determined that mono-n-butyl-tin-trichloride was obtained in yield of 55%.

EXAMPLE 4

The same operations as in Example 3 were repeated using 110 g of n-octyl chloride (n-C$_8$H$_{17}$Cl) in place of n-butyl chloride. Mono-n-octyl-tin-trichloride was obtained in yield of 40%.

EXAMPLE 5

The same procedures as in Example 1 were carried out using n-butyl alochol in place of tetrahydrofuran. Monomethyl-tin-trichloride was obtained in yield of 60%.

EXAMPLE 6

A reaction mixture was prepared from 50 g of stannous chloride, 60 g of toluene, 8 g of iodine, 0.5 g of magnesium and 50 g of methyl chloride. The reaction mixture was heated in a closed vessel at a temperature of 210° to 220° C for about 3 hours. After the completion of the reaction, the reaction mixture was filtered and then distilled at a temperature of 160° C under a reduced pressure of 60 mmHg while being stirred. As a result of a gas chromatographic analysis of the distillation residue, it was determined that monomethyl-tin-trichloride was obtained in an yield of 92%.

EXAMPLE 7

Procedures identical to those in Example 6 were repeated using 60 g of xylene in place of toluene. The yield of monomethyl-tin-trichloride was 81%.

EXAMPLE 8

The same procedures as those in Example 6 were effected using 50 g of n-hexane in place of toluene. The yield of monomethyl-tin-trichloride was 67%.

EXAMPLE 9

The same operations as in Example 6 were repeated using a Grignard reagent of the formula $C_4H_9mgBr$ in MgBr of iodine. Monomethyl-tin-trichloride was obtained in a yield of 85%.

EXAMPLE 10

A reaction mixture was prepared from 50 g of stannous chloride, 80 g of toluene, 10 g of iodine, 1 g of magnesium and 150 g of n-octyl chloride (n-$C_8H_{17}Cl$). The reaction mixture was heated in a closed vessel at a temperature of 220° to 230° C for 3 hours while being stirred. The reaction mixture was filtered and then distilled at a temperature of 180° C under a reduced pressure of 50 mmHg in order to remove the solvent and non-reacted n-octyl chloride. As a result of a gas chromatographic analysis of the distillation residue, it was determined that mono-n-octyl-tin-trichloride was obtained in a yield of 51%.

EXAMPLE 11

Procedures identical to those in Example 10 were effected using 120 g of n-butyl chloride in place of n-octyl chloride. Mono-n-butyl-tin-trichloride (n-$C_4H_9SnCl_3$) was obtained in a yield of 72%.

EXAMPLE 12

Procedures identical to those in Example 10 were carried out using 50 g of stannous bromide in place of stannous chloride, 10 g of bromide in place of iodine and 150 g of n-octyl bromide instead of n-octyl chloride. Mono-n-octyl-tin-tribromide was obtained in a yield of 66%.

EXAMPLE 13

A reaction mixture which had been prepared from 50 g of stannous chloride, 80 g of toluene, 10 g of iodine and 60 g of methyl chloride, was heated in a closed vessel at a temperature of 215° to 225° C for 3 hours while being vigorously stirred. After the reaction was completed, the reaction mixture was filtered and the filtrate was distilled at a temperature of 170 under a reduced pressure of 50 mmHg. The distillation residue was analyzed by way of gas chromatography. As a result, it was determined that monomethyl-tin-trichloride ($CH_3SnCl_3$) was present in a yield of 55%.

What we claim is:

1. A method for producing monoalkyl-tin-trihalides comprising reacting a stannous halide of the formula $SnX_2$ wherein X is selected from the group consisting of chlorine and bromine, with an alkyl halide of the formula RX wherein R is an alkyl group having 1 to 8 carbon atoms and X is selected from the group consisting of chlorine and bromine, in an organic solvent consisting of a mixture of tetrahydrofuran and an aromatic hydrocarbon having 6 to 9 carbon atoms, in the presence of a catalyst consisting of iodine and magnesium, and isolating said resulting monoalkyl-tin-trihalide from the reaction mixture.

2. A method as claimed in claim 1, wherein said alkyl halide is present in an amount by mole not smaller than that of said stannous halide.

3. A method as claimed in claim 1, wherein said organic solvent is present in an amount between 80 and 200% based on the sum of the weights of said stannous halide and said alkyl halide.

4. A method as claimed in claim 1, wherein said catalytic substance is present in an amount between 2 and 10% based on the sum of the weights of said stannous halide and said alkyl halide.

5. A method as claimed in claim 1, wherein said reaction is effected at a temperature of 150° to 250° C.

6. A method as claimed in claim 1, wherein said reaction is carried out at at least ambient pressure.

7. A method as claimed in claim 1, wherein said organic solvent has a boiling point of 60° through 200° C under 1 atmosphere of pressure.

8. A method as claimed in claim 1 wherein said aromatic hydrocarbons are selected from the group consisting of benzene, toluene, p-xylene, m-xylene, o-xylene and ethyl benzene.

* * * * *